(12) United States Patent
Sedic

(10) Patent No.: US 11,596,275 B2
(45) Date of Patent: *Mar. 7, 2023

(54) SKIN CLEANSER

(71) Applicant: FOREO Inc., Las Vegas, NV (US)

(72) Inventor: Filip Sedic, Shanghai (CN)

(73) Assignee: FOREO Inc., Las Vegas, NV (US)

(*) Notice: Subject to any disclaimer, the term of this patent is extended or adjusted under 35 U.S.C. 154(b) by 367 days.

This patent is subject to a terminal disclaimer.

(21) Appl. No.: 17/087,887

(22) Filed: Nov. 3, 2020

(65) Prior Publication Data
US 2021/0045590 A1    Feb. 18, 2021

Related U.S. Application Data

(63) Continuation of application No. 16/429,394, filed on Jun. 3, 2019, now Pat. No. 10,856,705, which is a
(Continued)

(51) Int. Cl.
A47K 7/02      (2006.01)
A61H 7/00     (2006.01)
(Continued)

(52) U.S. Cl.
CPC ............... A47K 7/02 (2013.01); A47K 7/04 (2013.01); A47K 7/043 (2013.01); A61B 5/443 (2013.01);
(Continued)

(58) Field of Classification Search
CPC .... A61H 2201/5097; A61H 2201/0153; A61H 23/02; A61H 7/003; A61H 7/005;
(Continued)

(56) References Cited

U.S. PATENT DOCUMENTS 1,491,016 A    4/1924  McGowan et al.
2,480,023 A    8/1949  Holden
(Continued)

FOREIGN PATENT DOCUMENTS

CN    2040777    7/1989
CN    2172110    7/1994
(Continued)

OTHER PUBLICATIONS

"Silicone Face Massage Brush," Alibaba.com, 1999-2014, Alibaba.com, 6 pages [Online] [Retrieved on Sep. 15, 2014] Retrieved from the Internet<URL:http://www.alibaba.com/countrysearch/CN/silicone-face-massage-brush.html.
(Continued)

Primary Examiner — Diane D Yabut
Assistant Examiner — Christina C Lauer
(74) Attorney, Agent, or Firm — Evan Feldstein

(57) ABSTRACT

A skin cleanser includes a surface, such as a silicone surface, with at least one textured portion for transmitting vibrational tapping to the skin. The skin cleanser includes at least one oscillating motor for generating the tapping motion to the skin. The textured portion in touch-points or a wave that transmit the tapping motion to skin in contact with the to portions. The touch-points may include thicker and thinner formations of the touch-points to provide firmer or softer vibrations to the skin. The touch-points are within about 0.5 to 2.5 mm in diameter. One configuration includes multiple oscillating motors configured to provide different vibration frequencies at around 50-300 Hertz and operable simultaneously.

20 Claims, 17 Drawing Sheets

Related U.S. Application Data continuation of application No. 16/295,446, filed on Mar. 7, 2019, now Pat. No. 10,349,788, which is a continuation of application No. 16/007,078, filed on Jun. 13, 2018, now Pat. No. 10,716,437, which is a continuation of application No. 15/893,971, filed on Feb. 12, 2018, now Pat. No. 10,028,884, which is a continuation of application No. 15/397,976, filed on Jan. 4, 2017, now Pat. No. 9,889,065, which is a continuation of application No. 14/572,519, filed on Dec. 16, 2014, now Pat. No. 10,213,064, which is a continuation of application No. 14/149,793, filed on Jan. 7, 2014, now Pat. No. 9,907,439.

(60) Provisional application No. 61/841,542, filed on Jul. 1, 2013, provisional application No. 61/749,751, filed on Jan. 7, 2013.

(51) Int. Cl.
- A61H 23/00 (2006.01)
- A61H 23/02 (2006.01)
- A61B 5/00 (2006.01)
- A47K 7/04 (2006.01)

(52) U.S. Cl.
CPC .............. *A61B 5/445* (2013.01); *A61H 7/002* (2013.01); *A61H 7/003* (2013.01); *A61H 7/004* (2013.01); *A61H 7/005* (2013.01); *A61H 23/00* (2013.01); *A61H 23/006* (2013.01); *A61H 23/02* (2013.01); *A61H 23/0254* (2013.01); *A61H 23/0263* (2013.01); *A61H 2023/0272* (2013.01); *A61H 2201/0153* (2013.01); *A61H 2201/0157* (2013.01); *A61H 2201/02* (2013.01); *A61H 2201/0207* (2013.01); *A61H 2201/105* (2013.01); *A61H 2201/1215* (2013.01); *A61H 2201/1223* (2013.01); *A61H 2201/5002* (2013.01); *A61H 2201/5035* (2013.01); *A61H 2201/5038* (2013.01); *A61H 2201/5041* (2013.01); *A61H 2201/5097* (2013.01); *A61H 2205/022* (2013.01)

(58) Field of Classification Search
CPC .......... A61H 23/00; A61H 19/40; A47K 7/04; A47K 7/043; A47K 7/02; A47L 13/16
See application file for complete search history.

(56) References Cited

U.S. PATENT DOCUMENTS

| | | | |
|---|---|---|---|
| 2,764,773 A | 10/1956 | Glanvill et al. |
| 2,867,211 A | 1/1959 | Hughes |
| 3,251,085 A | 5/1966 | Jacobs |
| 3,346,748 A | 10/1967 | Mcnair |
| 3,358,309 A | 12/1967 | Richardson |
| 3,906,940 A | 9/1975 | Kawada |
| 3,968,789 A | 7/1976 | Simoncini |
| 4,027,348 A | 6/1977 | Flowers et al. |
| 4,112,040 A | 9/1978 | Orentreich |
| 4,249,521 A | 2/1981 | Gueret |
| 4,463,485 A | 8/1984 | Gueret |
| 4,564,032 A | 1/1986 | Araki |
| 4,570,616 A | 2/1986 | Kunz et al. |
| D288,847 S | 3/1987 | Kaeser |
| D331,466 S | 12/1992 | Doria |
| 5,176,130 A | 1/1993 | Kim |
| D351,474 S | 10/1994 | Huang |
| D361,386 S | 8/1995 | Vandenbelt |
| D369,220 S | 4/1996 | Huang |
| 5,511,270 A | 4/1996 | Eliachar et al. |
| D382,645 S | 8/1997 | Bergeron |
| 5,792,080 A | 8/1998 | Ookawa et al. |
| D423,109 S | 4/2000 | Allende |
| 6,202,242 B1 | 3/2001 | Salmon et al. |
| 6,226,811 B1 | 5/2001 | Fagan |
| 6,267,736 B1 | 7/2001 | McCambridge et al. |
| 6,283,930 B1 | 9/2001 | Purvis et al. |
| D456,942 S | 5/2002 | Au et al. |
| 6,393,718 B1 | 5/2002 | Harris et al. |
| 6,432,072 B1 | 8/2002 | Harris et al. |
| D466,217 S | 11/2002 | Harris et al. |
| D466,695 S | 12/2002 | Chen |
| D469,183 S | 1/2003 | Gerth et al. |
| D476,087 S | 6/2003 | Dirks et al. |
| 6,588,964 B1 | 7/2003 | Au et al. |
| D478,174 S | 8/2003 | Huang |
| D487,592 S | 3/2004 | Chang |
| D512,225 S | 12/2005 | Chien |
| D514,328 S | 2/2006 | Huang |
| D517,218 S | 3/2006 | Kalen |
| D523,561 S | 6/2006 | Telford |
| D523,958 S | 6/2006 | Fang |
| D539,917 S | 4/2007 | Park |
| D548,851 S | 8/2007 | Huang |
| D549,351 S | 8/2007 | Wu |
| D557,806 S | 12/2007 | Gromosaik et al. |
| 7,303,534 B2 | 12/2007 | Kahn |
| 7,320,691 B2 | 1/2008 | Pilcher et al. |
| D569,106 S | 5/2008 | Maruyama |
| D571,926 S | 6/2008 | Wu |
| 7,384,377 B2 | 6/2008 | Berman |
| D574,108 S | 7/2008 | Yando et al. |
| D576,736 S | 9/2008 | Hagege |
| D595,898 S | 7/2009 | Syran et al. |
| D616,103 S | 5/2010 | Ford-Robertson |
| D622,405 S | 8/2010 | Tuli |
| D626,656 S | 11/2010 | Jarry |
| D629,528 S | 12/2010 | Adkisson |
| D635,720 S | 4/2011 | Cammarano |
| D645,569 S | 9/2011 | Nitsch |
| D646,795 S | 10/2011 | Seehoff et al. |
| D648,442 S | 11/2011 | Caggiano |
| D652,525 S | 1/2012 | Caggiano |
| D652,941 S | 1/2012 | Zamar |
| D671,281 S | 11/2012 | Singer |
| D674,108 S | 1/2013 | York |
| 8,523,791 B2 | 9/2013 | Castel |
| 8,622,890 B1 | 1/2014 | Caggiano et al. |
| 8,679,039 B2 | 3/2014 | Tieu et al. |
| 8,745,807 B2 | 6/2014 | Varner et al. |
| D715,935 S | 10/2014 | Huntington et al. |
| D768,391 S | 10/2016 | Kling et al. |
| 9,889,065 B2 * | 2/2018 | Sedic ................ A61H 23/0263 |
| 10,028,884 B2 * | 7/2018 | Sedic .................... A61H 23/00 |
| 10,213,064 B2 * | 2/2019 | Sedic .................... A61B 5/445 |
| 10,349,788 B1 * | 7/2019 | Sedic ...................... A47K 7/04 |
| 10,716,437 B2 * | 7/2020 | Sedic ...................... A47K 7/02 |
| 10,856,705 B2 * | 12/2020 | Sedic .................... A61B 5/445 |
| 10,973,374 B1 * | 4/2021 | Sedic .................... A61B 5/443 |
| 2002/0107459 A1 | 8/2002 | Chang |
| 2004/0060571 A1 | 4/2004 | Mayeri |
| 2004/0225239 A1 | 11/2004 | Yamamoto et al. |
| 2005/0059914 A1 | 5/2005 | Kleinhenz et al. |
| 2005/0113725 A1 | 6/2005 | Masuda |
| 2005/0142093 A1 | 6/2005 | Skover et al. |
| 2006/0010630 A1 | 3/2006 | Tse |
| 2006/0058714 A1 | 8/2006 | Rhoades |
| 2006/0236474 A1 | 10/2006 | Jaffe |
| 2006/0168746 A1 | 12/2006 | Guyuron et al. |
| 2006/0276731 A1 | 12/2006 | Thiebaut et al. |
| 2007/0017540 A1 | 1/2007 | Davis et al. |
| 2007/0142845 A1 | 6/2007 | Akridge et al. |
| 2007/0179412 A1 | 8/2007 | Imboden et al. |
| 2007/0198031 A1 | 8/2007 | Kellogg |
| 2007/0232967 A1 | 10/2007 | Driscoll |
| 2008/0110471 A1 | 5/2008 | Oliver et al. |
| 2008/0119913 A1 | 5/2008 | Powell et al. |
| 2008/0125680 A1 | 5/2008 | Richmond et al. |
| 2008/0125682 A1 | 5/2008 | Bonneyrat |

(56) References Cited

U.S. PATENT DOCUMENTS

| | | |
|---|---|---|
| 2008/0167590 A1 | 7/2008 | Jon et al. |
| 2008/0210252 A1 | 9/2008 | Taggart et al. |
| 2009/0036809 A1 | 2/2009 | Nishio et al. |
| 2009/0198159 A1 | 8/2009 | Linzell |
| 2009/0275796 A1 | 11/2009 | Gil |
| 2009/0312599 A1 | 12/2009 | Smith |
| 2009/0318755 A1 | 12/2009 | Adams et al. |
| 2009/0318853 A1 | 12/2009 | Reed et al. |
| 2010/0036295 A1 | 2/2010 | Altshuler et al. |
| 2010/0217357 A1 | 8/2010 | Da Silva et al. |
| 2010/0262051 A1 | 10/2010 | De LaForcade |
| 2011/0071445 A1 | 3/2011 | Imboden |
| 2011/0087141 A1 | 4/2011 | Wagy et al. |
| 2011/0098613 A1 | 4/2011 | Thomas et al. |
| 2011/0144426 A1 | 6/2011 | Blenk et al. |
| 2011/0184499 A1 | 7/2011 | Radi |
| 2011/0251537 A1 | 10/2011 | Yeo |
| 2011/0257474 A1 | 10/2011 | Howard |
| 2011/0270274 A1 | 11/2011 | Hull |
| 2012/0121313 A1 | 5/2012 | Thiebaut |
| 2012/0165708 A1 | 6/2012 | Parsloe |
| 2012/0209151 A1 | 8/2012 | Zhou et al. |
| 2012/0234336 A1 | 9/2012 | Paquet et al. |
| 2013/0023805 A1 | 1/2013 | Ungemach et al. |
| 2013/0046212 A1 | 2/2013 | Nichols |
| 2013/0079689 A1 | 3/2013 | Thierman |
| 2013/0178769 A1 | 7/2013 | Schmidt |
| 2014/0046127 A1 | 2/2014 | Topolovac et al. |
| 2014/0107543 A1 | 4/2014 | Pazouki |
| 2014/0171841 A1 | 6/2014 | Kazaryan et al. |
| 2014/0296626 A1 | 10/2014 | Butler et al. |
| 2022/0133096 A1* | 5/2022 | Sedic .................. A61H 23/00 606/131 |

FOREIGN PATENT DOCUMENTS

| | | |
|---|---|---|
| CN | 1655709 | 8/2005 |
| CN | 2761119 | 3/2006 |
| CN | 101056603 | 10/2007 |
| CN | 201422994 | 3/2010 |
| CN | 2012637712 | 1/2013 |
| CN | 302512535 | 7/2013 |
| CN | 302512536 | 7/2013 |
| EP | 1484043 | 12/2004 |
| EP | 1525872 | 4/2005 |
| EP | 1942857 | 7/2008 |
| EP | 2164443 | 3/2010 |
| EP | 2490645 | 8/2012 |
| JP | 2000-000283 | 1/2000 |
| JP | 2004-249061 | 9/2004 |
| KR | 101078567 | 1/2011 |
| TW | 200410650 | 7/2004 |

OTHER PUBLICATIONS

United States Office Action, U.S. Appl. No. 14/572,519, filed Jul. 18, 2016, twelve pages.
"Clarisonic" Web Page, Clarisonic, Pacific Bioscience Laboratories, Inc., 2013, 2 pages, [Online] [Retrieved on Sep. 15, 2014] Retrieved from the Internet<URL: http://www.clarisonic.com/>.
"Neutrogena® Wave®," Neutrogena Corporation, 2014, 1 page, [Online] [Retrieved on Sep. 15, 2014] Retrieved from the Internet<URL:http://www.neutrogenawave.com/#/products>.
"Silicon Face Brushes," Alibaba.com, 1999-2014, Alibaba.com, 8 pages [Online] [Retrieved on Sep. 15, 2014] Retrieved from the Internet<URL:http://www.alibaba.com/manufacturers/face-silicone-brush-manufacturer.html>.
"Vibrating cosmetics," 12 pages, PoshGlam®, Sep. 8, 2014, [Online] [Retrieved on Sep. 15, 2014] Retrieved from the Internet<URL:http://www.poshglam.com/beauty/>.
"Waterproof Electric Face Massager," Alibaba.com, 1999-2014, 3 pages, [Online] [Retrieved on Sep. 15, 2014] Retrieved from the Internet<URL:http://www.alibaba.com/product-gs/537532136/Water_proof_Electric_Face_Massager.html>.
Australian Government, IP Australia, Patent Examination Report No. 1, Australian Patent Application No. 2014204242, dated Jan. 28, 2016, three pages.
European Extended Search Report, European Application No. 14735118.3, dated Jun. 7, 2016, ten pages.
FOREO: Building the Best Brand of Skin Care, Dec. 13, 2013 [online], retrieved on Aug. 26, 2014}. Retrieved from the Internet: <http://luxury.ce.cn/hydt/cygc/201312/13/t20131213_1271555.shtml>.
Global First Silicone Cleansing Instrument FOREO Leading a New Revolution 1-19 in Facial Care, Jun. 28, 2013 [online], [retrieved on Aug. 26, 2014). Retrieved from the Internet: <http://fashion.ifeng.com/news/detail_2013_06/28/26922193_0.shtml>.
Japan Patent Office, Office Action, Japanese Patent Application No. 2016-006716, dated Jul. 29, 2016, five pages.
Japan Patent Office, Office Action, Japanese Patent Application No. 2016-006717, dated Jul. 29, 2016, five pages.
PCT International Search Report and Written Opinion, PCT Application No. PCT/IB2014/000530, dated Oct. 22, 2014, eight pages.
Science Share: Share the Tutorials of Electric Washing Device FOREO, Nov. 20, 2013 [online], [retrieved on Aug. 26, 2014). Retrieved from the Internet: <http://bbs.pclady.com.cn/topic-1782404.html> (with concise explanation of relevance).
Silicone Suction Cup Face Exfoliate Beauty Brushes, SourcingMap Ltd., 2006-2014, two pages, [Online] [Retrieved on Sep. 15, 2014] Retrieved from the Internet<URL: http://www.sourcingmap.com/ladies-silicone-suction-cup-face-exfoliate-beauty-brushes-pink-p-242745.html>.
United States Office Action, U.S. Appl. No. 14/149,793, dated Apr. 21, 2016, twenty-five pages.
United States Office Action, U.S. Appl. No. 14/572,519, dated Mar. 27, 2015, ten pages.
United States Office Action, U.S. Appl. No. 14/149,793, dated Sep. 24, 2015, twenty-seven pages.
United States Office Action, U.S. Appl. No. 14/572,519, dated Dec. 16, 2016, 13 pages.
United States Office Action, U.S. Appl. No. 15/397,976, dated Feb. 8, 2017, 40 pages.
United States Office Action, U.S. Appl. No. 15/397,976, dated Mar. 21, 2017, 16 pages.
United States Office Action, U.S. Appl. No. 15/397,976, dated May 23, 2017, 24 pages.
United States Office Action, U.S. Appl. No. 14/149,793, dated Feb. 9, 2017, 32 pages.
SIPO of the People's Republic of China, Second Office Action, Chinese Pat. App. No. 201480010001.2, dated Aug. 23, 2017, 10 pages.
United States Office Action, U.S. Appl. No. 14/572,519, dated May 9, 2017, pp. 1-9.
United States Office Action, U.S. Appl. No. 14/572,519, dated Sep. 26, 2017, pp. 1-8.
State Intellectual Property Office (China), Intl. App. No. 20140010001.2, First Office Action, dated Feb. 23, 2017, pp. 1-11.
United States Office Action, U.S. Appl. No. 14/149,793, dated Jun. 2, 2017, pp. 1-30.
Australian Government, IP Australia, Examination Report No. 1 for Australian Patent Application No. AU 2016262690, dated Sep. 27, 2017, 3 pages.
3rd Office Action for Chinese Patent Application No. CN 201480010001.2, dated Apr. 11, 2018, 9 pages.
IP Australia, "Examination Report No. 2 for Innovation Patent," Int. App. No. 2017100130, dated Aug. 11, 2017, pp. 1-5.
European Patent Office, Examination Report, European Patent Application No. 14735118.3, dated Aug. 29, 2017, 6 pages.
SIPO of the People's Republic of China, Fourth Office Action, Chinese Pat. App. No. 201480010001.2, dated Nov. 7, 2018, 6 pages.
CIPO, Office Action, Int'l app. No. 2,897,177, dated Feb. 25, 2019, pp. 1-4.
USPTO, "Non-final Office Action," dated Apr. 23, 2020, U.S. Appl. No. 16/007,078, pp. 1-55.

(56) References Cited

OTHER PUBLICATIONS

TechFever Network, techfever.com, "FOREO's Luna mini Promises to Bring Tech to Skincare," pp. 1-2, Jan. 11, 2013, http:www.techfever.net/2013/01/ces-2013-foreos-luna-mini-promises-to-bring-tech-to-skincare/.

EPO, "Summons to attend oral proceedings," Int'l app. 14735118.3., dated Nov. 4, 2019, pp. 1-11.

EUIPO, "Extended EU Search Report," app. No. 20212059.8, pp. 1-10.

\* cited by examiner

SKIN CLEANSER

CROSS REFERENCE TO RELATED APPLICATIONS

This application is a continuation of Non-provisional U.S. patent application Ser. No. 16/429,394, filed Jun. 3, 2019, which is a continuation of Non-provisional U.S. patent application Ser. No. 16/295,446, filed Mar. 7, 2019, which is a continuation of Non-provisional U.S. patent application Ser. No. 16/007,078, filed Jun. 13, 2018, which is a continuation of Non-provisional U.S. patent application Ser. No. 15/893,971, filed Feb. 12, 2018, which is a continuation of Non-provisional U.S. patent application Ser. No. 15/397,976, filed Jan. 4, 2017, which is a continuation of Non-provisional U.S. patent application Ser. No. 14/572,519, filed Dec. 16, 2014, which is a continuation of Non-provisional U.S. patent application Ser. No. 14/149,793, filed Jan. 7, 2014, which claims the benefit of U.S. Provisional Application No. 61/749,751, filed Jan. 7, 2013, and U.S. Provisional Application No. 61/841,542, filed Jul. 1, 2013. Each of these related applications is incorporated by reference into this disclosure in its entirety.

BACKGROUND

Skin health and appearance is an important aspect of many beauty regimens. Typical skin care focuses on particular creams or lotions to be applied to the skin, usually performed manually by sponge or brush. Cleaning by hand often fails to adequately apply lotions to the skin, and can be ineffective at removing grease, oils, and other contaminants. An effective skin cleanser device should clean the face more effectively than hand cleaning, but avoid abrasions or other harsh impacts on the skin.

SUMMARY

A skin cleanser includes one or more oscillating motors or other electromagnetic device that can provide the skin cleanser with various frequency pulsations, and an exterior that can be composed of a soft elastic material, such as silicone, and one or more textured surfaces, including rounded touch-points of 0.5 to 2.5 mm of diameter, or solid surfaces with ridges for cleaning or otherwise interacting with the skin. The oscillating motor moves or oscillates the textured surfaces for application to a user's skin. As the user moves the skin cleanser on the skin, the oscillating pulsations combined with the textured surfaces' touch-points remove oil and other contaminants on the skin's surface. The oscillating pulsations provide a tapping motion to the user's skin to cleanse and loosen contaminants. The oscillations occur at around 50-300 Hertz (Hz). One embodiment includes a high-frequency and a low-frequency oscillating motor or other electromagnetic device that may operate simultaneously or independently. The simultaneous pulsations provide a deep cleaning to the skin. While referred to here as a skin cleanser, the device can also perform other functions besides cleansing, including massaging, exfoliating, buffing, stimulating, toning, exercising, heating, applying lotions or other substances, and so forth.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Figure 1:
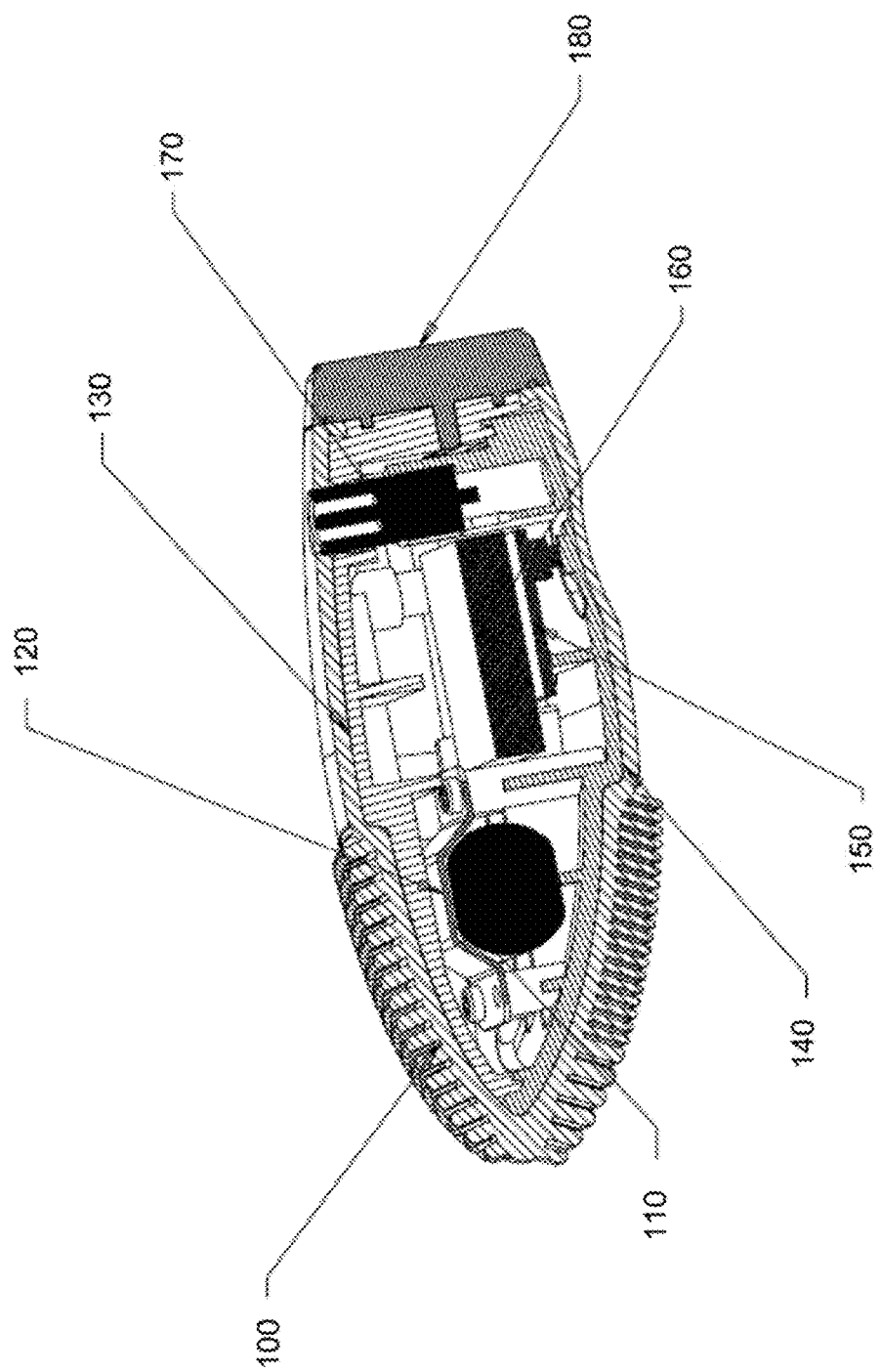
FIG. 1 is a cross-sectional view of a skin cleanser, according to one embodiment.

FIG. 1 is a cross-sectional view of a skin cleanser, according to one embodiment. The skin cleanser directs pulsations to a user through rounded touch-points on a brush, such as silicone brush 100. The touch-points and brush can be composed of various elastic materials, preferably materials that are soft and do not damage the skin, such as silicone. Silicone is used as an example throughout, though it is understood that other materials can be used, as well. The silicone brush 100 is made of a hygienic silicone that is fast-drying and non-absorbent, allowing the skin cleanser to be used with many skin cleaning products without wear. The silicone brush 100 and other user-contacting portions of the skin cleanser may also include active ingredients, such as vitamin E, antioxidants, or silver nanoparticles. For example, the can be coated with these ingredients by the user or pre-coated, or can have a delivery mechanism in the brush that can store and provide these ingredients upon use. A high- or low-frequency oscillating motor 110 creates pulsations that vibrate the skin cleanser. The oscillating motor 110 in this embodiment provides vibrations between 50 and 300 Hz, though pulsation frequencies higher and lower than this range may also provide beneficial cleansing of the skin. When the skin cleanser, and the silicone brush 100 in particular, is applied to the body, such as the face or neck, the pulsations provide a thorough cleaning of the skin. The pulsations provide a tapping motion to the skin, in some embodiments, by providing impulses to the skin's surface from the silicone touch-points 100 pulsating against the skin's surface. The tapping-based cleansing provided by the silicone brush provides a deeper clean that is less abrasive than scrubbing the skin with harsher bristles of other materials (e.g., nylon brush bristles). Frequencies in this range provide deep facial cleansing of oil and dirt, unclog follicles, and stimulate blood circulation and lymph flow within the skin.

The oscillating motor 110 is enclosed in a frame 120, which is enclosed by a casing including a top 130 and a bottom 140 made of a suitable material, such as plastic. In some embodiments, there is more than one oscillating motor, which may vary from one another in frequency. A controller, such as a printed circuit board 150, provides control to the oscillating motor 110, which is powered by a battery 160. The battery 160 is charged through a charging port, such as a DC jack 170.

The user interacts with the controller through controls on the exterior of the skin cleanser (such as those shown in FIG. 3) or through a wireless remote. When activated by the controls, the controller initiates a high-frequency vibration of the oscillating motor 110. The user may increase and decrease the frequency of vibration of the motor through controls to set the frequency desired by the user. The frequency set by the user may be stored by the controller when the controller is deactivated, such that the next time the controller is turned on the controller resumes the desired frequency.

Figure 2:
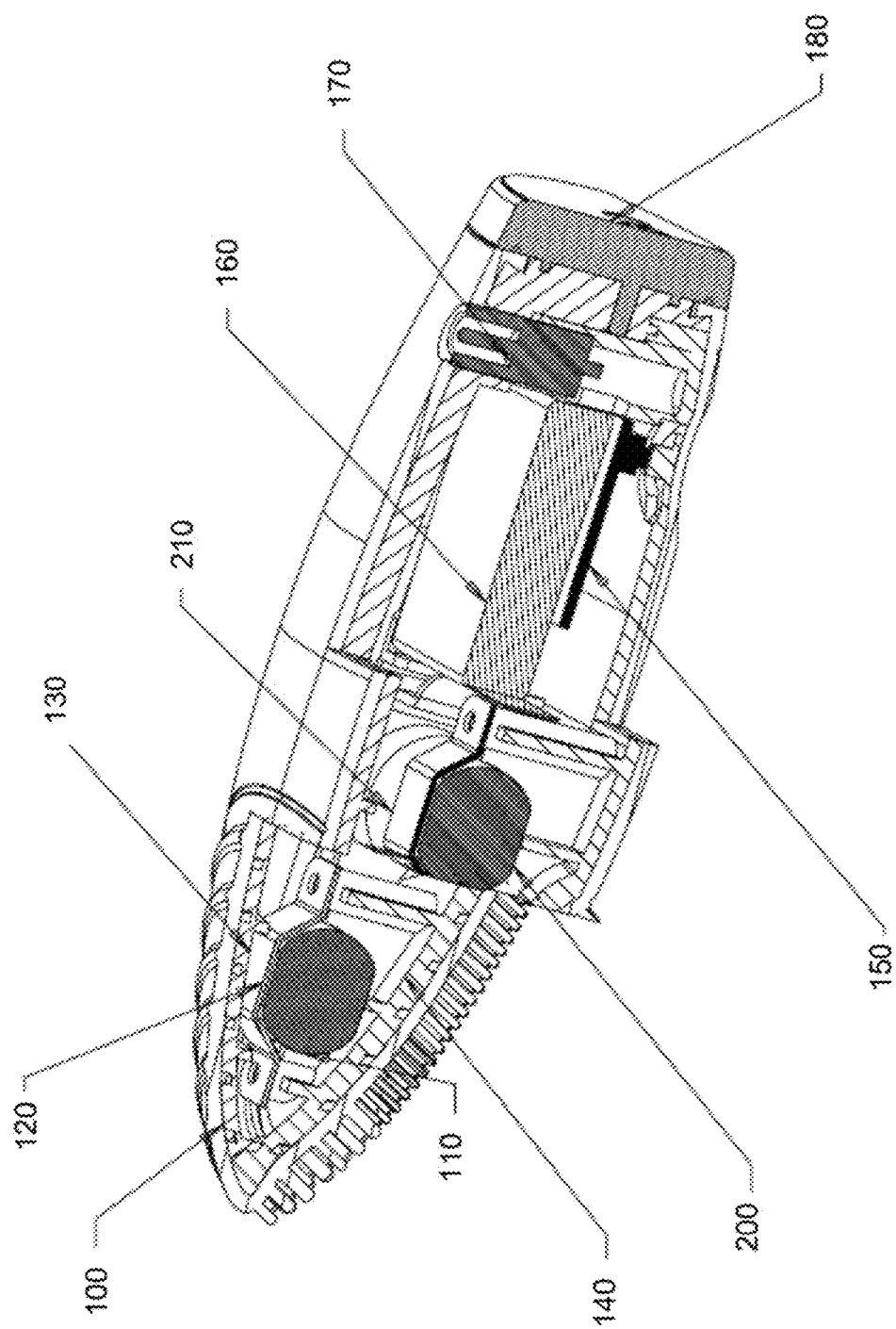
FIG. 2 is a cross-sectional view of a skin cleanser, according to one embodiment.

FIG. 2 is a cross-sectional view of a skin cleanser, according to one embodiment. The skin cleanser in FIG. 2 includes similar components to the skin cleanser in FIG. 1, and additional components as described. This embodiment includes a second oscillating motor 200 and a frame 210 containing the second motor 200. In this embodiment, the second motor 200 is capable of creating vibrations at a lower frequency relative to the high-frequency oscillating motor 110. The second motor 200, for example, produces pulsations of 50-130 Hz. The controller in this embodiment may use the second motor 200 alone or in combination with the high-frequency motor 110 to create different vibration effects from the skin cleanser. Using the back-side of the brush, upward strokes on the skin, such as beneath the jaw line, allow the stronger combination of high-frequency and lower-frequency vibration to tone and tighten underlying musculature, such as that of the neck. Additional benefits can range from stimulating collagen synthesis in fibroblast cells to improving the flow of blood and lymphatic fluid—the result is healthier, younger-looking skin, such as in the known problem areas of the face, and a more sharply defined profile of the face. In one embodiment, the FIG. 2 device is a larger cleanser and the FIG. 1 device is a smaller or mini-cleanser.

The controller may also activate the lower-frequency motor alone. The lower-frequency vibrations (e.g., in the range of 50-130 Hertz) in conjunction with ridged silicone brush may be used by a user on the skin to relax underlying musculature. In particular, when gently applied to expression-line problem areas at the brow, temples and nasolabial folds, the skin cleanser can relax underlying muscles and reduce the appearance of dynamic wrinkles. Thus, the high-frequency oscillating motor 110 together with the second oscillating motor 200 may enable the skin cleanser to provide a variety of modes and benefits to the user. In some embodiments, the motors 110, 200 can be used in an alternating fashion to provide alternating low and high frequency pulsations to the cleanser.

In one embodiment, a sensor is also included in the skin cleanser near the front or back of the skin cleanser (or both). The sensor may be a pressure sensor, capacitive sensor, or similar, and detects a user's action to activate the sensor, such as by contacting the body exterior to the sensor. In one embodiment, the controller activates at least one of the oscillating motors when the sensor is activated, permitting the device to automatically activate when the user activates the sensor. Multiple sensors may be included to activate different functions. For instance, in one configuration a sensor is located underneath each textured side of the skin cleanser and detects contact with that textured side. Based on which sensor is activated, the controller activates an operational mode suitable for the side on which the sensor was activated. For example, activating only the low-frequency oscillating motor when one side is contacted, and simultaneously activating the low- and high-frequency oscillating motors when the other side is contacted.

FIGS. 3-9 illustrate various views of the exterior of a skin cleanser according to some embodiments. The exterior shown in FIGS. 3-9 correspond to the internal configuration shown in FIG. 2. The exterior is formed of a sort but durable elastic material, such as a hygienic silicone. The skin cleanser includes brush surfaces 300 and 400 on the front and the back of the device with varying textures, such as touch-points of 0.5-2.5 mm diameter, or solid ridged surfaces. The brush surface 300 comprises a series of thinner touch-points for gentle cleansing of non-oily or sensitive skin, with an area of thicker touch-points grouped towards the top of the cleanser. Providing more resistance than the thinner touch-points, the thicker touch-points allow for more targeted cleansing of oilier areas and hard to-reach points around the nose, ears and hairline. The pattern of touch-points presented in FIGS. 3-9 is one example of a pattern that might be used to cleansing of what is commonly referred to as "normal"skin. Normal skin can include some areas that are drier, oilier, or more sensitive, such that the different patterns of thinner and thicker touch-points can be helpful in targeting these areas (e.g., thinner touch-points for oily areas around the nose). The thinner touch-points and thicker touch-points may vary in size and spacing. In various embodiments, the thinner touch-points are 25-80% thinner (e.g., 30%, 40%, 50%, 60%, 70%, etc. or values in between) compared to the thicker touch-points. In various embodiments, the thinner touch-points are spaced closer together (i.e., the distance between touch-points) by 15%-60%. Thus, the thinner and thicker touch-points for the normal skin cleansing can also be arranged differently around the brush surface than is shown in FIGS. 3-9. In one embodiment, the thicker touch points are between about 1.5 mm and 2.5 mm in diameter, and the thinner touch points are between about 0.5 mm and 1.5 mm in diameter.

The touch points and the body of the skin cleanser itself may be compressible and bendable, such that the touch points and body of the skin cleanser conform to the surface of the skin during use.

The brush surface 400 is a series of smooth silicone ridges arranged in a wave formation, intended to provide minimal abrasion and maximize the pulsation energy transfer, and the effectiveness of the dual-frequency toning and low-frequency, muscle-relaxing functions. Thus, both surfaces 300 and 400 of the brush can be used for skin cleansing, and specifically for different applications of skin cleansing.

The front of the skin cleanser also includes a mode control 310 and frequency controls 320. The mode control 310 activates the skin cleanser and is used to cycle through modes of operation for the skin cleanser, such as turning the cleanser on, activating the high-frequency and second lower-frequency motor both independently or in unison, and turning the skin cleanser off. Fewer, more, or different controls may be included for other embodiments. The skin cleanser may also activate a mode that directs the user to cycle through portions of the face when applying vibrations through the skin cleanser. The base 330 of the cleanser may light up or otherwise indicate a prompt for the user to move to another portion of the face. As one example, in this mode that directs cycling through the face, the cleanser may first indicate that the user should apply the brush to the area around the cheeks for a period of time, and then may indicate that the user should apply the brush to the area around the chin, and so forth until the user has cycled throughout the face. The cleanser can indicate when it is time to switch by, for example, lighting up the base, blinking the light a certain number of times, or otherwise using the light to indicate instructions to the user. Different cleaning regimens can be used for different cleansers. For example, a sensitive skin cleanser might have a cycle that is shorter in certain areas of the face to avoid irritating the face. A user might also have a program designed specifically for the user's own skin, with shorter or longer application of the brush to different areas of the face as needed for that user's skin. The program designed for a user's skin may be assessed by the manufacturer and programmed to the controller according to a diagnostic of the user's particular skincare needs.

The brush surfaces are designed to efficiently channel the high-frequency vibrations into the skin to cleanse deeply, unblock follicles, and to boost circulation and lymph flow. By avoiding abrasive exfoliation (as used in other brush-type devices), the brush surface remains gentle enough to use for twice-daily facial cleansing or more uses in the day, as needed. Relative to oilier cleansing devices, this skin cleanser does not rely on a spinning or twisting action; the result is a deeper clean without the need for such abrasive scrubbing. The pulsations in combination with the textured surfaces, the elastic, soft material touch-points and the solid ridged surfaces provide thorough cleansing, since (be textured surface directs the power of the high-frequency motor substantially orthogonal to the skin's surface, which unlocks the skin's natural potential. In one embodiment, the touch-points of the textured surface vertically oscillate from the brush to the skin to create a tapping motion on the skin, similar to the lapping of fingertips on the skin or the patting with a towel or cotton pad. The vertical tapping of the skin in this embodiment provides a gentle cleansing of the skin, as opposed to a rotating motion that can cause a less favorable twisting or stretching of the skin that may cause damage to or scratching of the skin surface.

The vertical tapping motion can be generated by the vibrations of the motor or of multiple motors, or other electromagnetic device in the brush, by electromechanical mechanisms, among other means. For example, the motors can be positioned in the brush to cause the vertical oscillations of the touch-points, such as by positioning one or more motors directly under or adjacent to the textured surface of the brush. The oscillation of the motor(s) can cause each of or at least some of the touch-points to move orthogonal to the skin's surface to tap the skin. Multiple motors can be arranged near the textured surface to create different motions or different speeds of vertical oscillations across the textured surface of the skin. For example, the motors can be positioned so that different touch-point arrangements or patterns on the textured surface can oscillate differently from one another to provide one type of tapping motion for some touch-points and a different type (e.g., different speed, pattern, etc.) for other touch-points. In some embodiments, each touch-point is a single structure rather than a plurality of structures, such as might be found in a brush where each brush bristle is made up of multiple bristle components arranged as a bunch.

The skin cleanser body can be configured to have different shapes, such as a substantially oval shape (e.g., FIGS. 3-9), a substantially round shape (e.g., FIGS. 17-18), and so forth, and it includes a base 330 that is substantially flat to allow the cleanser to be placed on and stand on a surface. The oval or round shape of the body allows the user to hold the cleanser in the palm of her hand, possibly with fingers splayed along the back side of the cleanser and thumb against the controls in the front side of the cleanser. In some embodiments, the cleanser is wider than it is thick, as is shown, for example, in FIG. 5. This configuration allows the user to easily hold the cleanser in the palm of her hand and reach her fingers around both side of the cleanser for easy and ergonomic manipulation of the cleanser against the skin. The body can thus have two components, the textured portions 300 and 400, and a handle or portion for grasping or manipulating the device, which includes everything other than the textured portions 300, 400. The textured portion can comprise at least 10%, 20%, 30%, 40%, 50% or more of the cleanser outer surface or of the front or of the back of the cleanser outer surface. The textured portion can be positioned on an upper portion or tip of the cleanser, such as is shown in FIGS. 3-9, but can also be otherwise positioned (e.g., at the sides, in the middle, at the bottom, etc.).

FIGS. 3-9 provide just one example of how the touch-points on the brush can be arranged. A variety of other arrangements are also possible (e.g., thinner touch-points at the top and thicker at the bottom, thinner on one side and thicker on the other side, alternating rows of thinner and thicker, various areas or groupings of thinner and thicker in different locations on the brush, and so forth). In addition, different types of touch-points can be included, such as taller or shorter touch-points, touch-points with more or less bulbous ends, touch-points with ends of different shapes (e.g., pointed, feathered, ridged, etc.), and so forth. Similarly, the touch-points can be arranged more or less densely, can be positioned on both the front and back of the brush, can be otherwise located on the brush (e.g., only in the middle, only at the edges, etc.), among other variations. Some other examples of touch-point arrangements are shown in FIGS. 10-15. In addition, the ridges of brush surface 400 in FIGS. 3-9 (and for FIGS. 10-15) can be arranged on one or both sides of the brash, can be otherwise located on the brush (e.g., only in the middle, only at the edges, etc.), can be positioned with the touch-points (e.g., above or below, or intermingled within the touch-points), can be formed into other patterns or shapes or with different spacing, among other variations.

Figure 10:
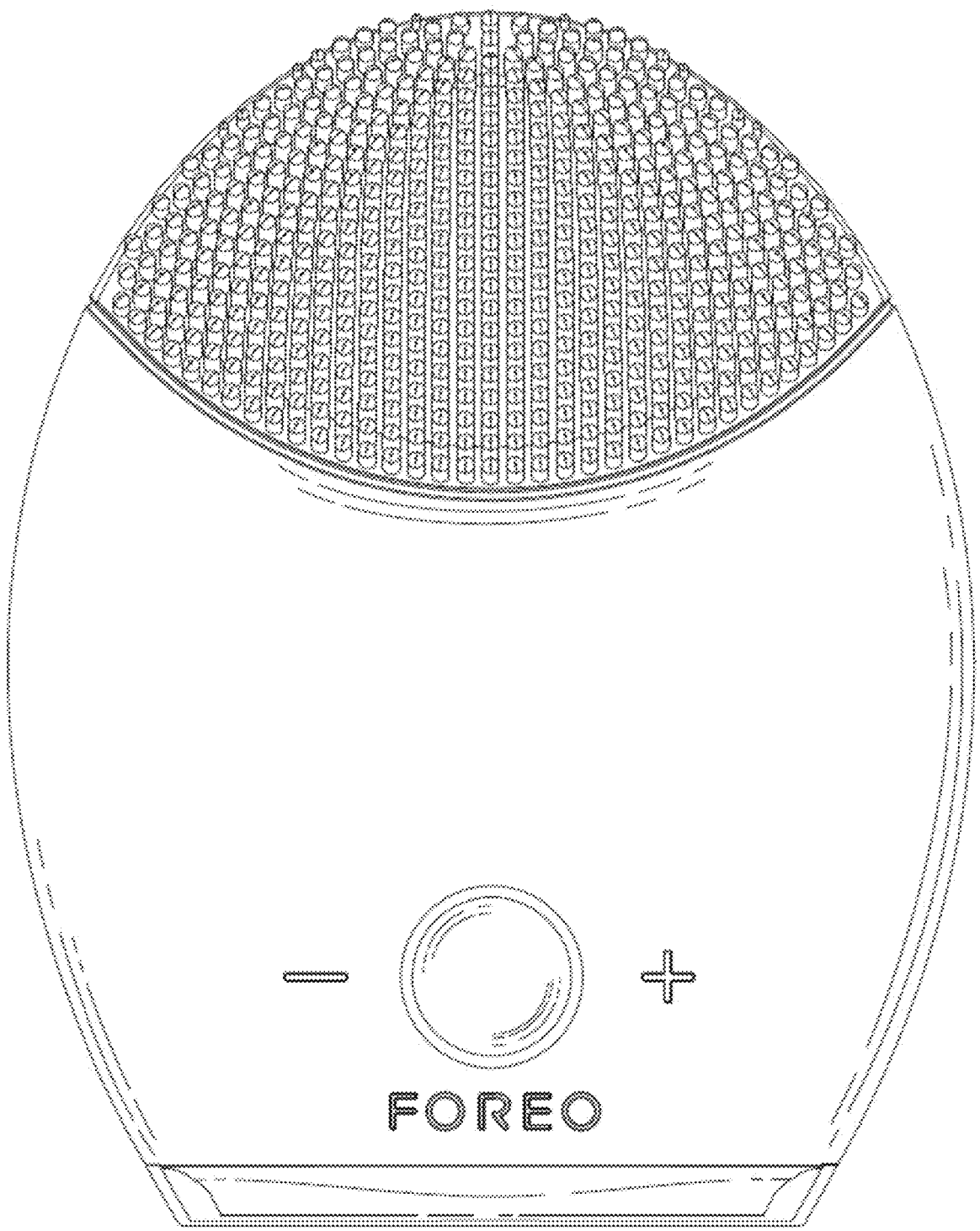
FIGS. 10 and 11 are views of one embodiment of a brash surface configuration for a skin cleanser.
Figure 11:
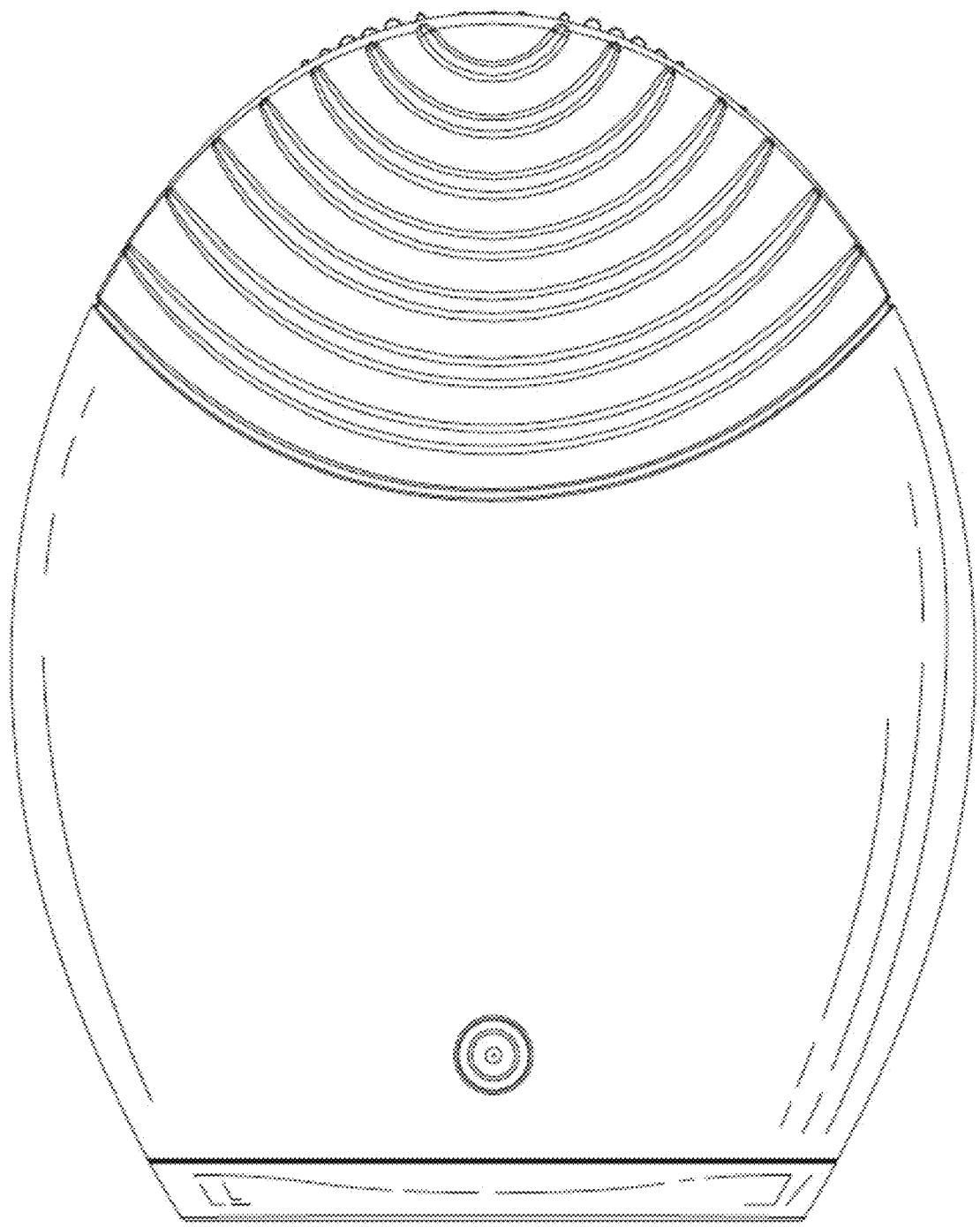

FIGS. 10 and 11 are views of one embodiment of a brush surface configuration for a skin cleanser. This brush configuration is specialized for men's facial skin. The brush on the front side, as shown in FIG. 10, includes a series of thicker touch-points covering the whole front surface, reflecting the additional cleansing normally required for men's oilier skin, with its larger pores and facial hair that act as magnets for dirt and pollutants, making acne, blackheads and breakouts more likely to occur. Providing more resistance than the thinner touch-points, they allow for firmer, deeper cleansing to meet the challenges of a man's thicker skin. The resulting boost to the health of the skin can reduce the discomfort and irritation often associated with, for example, daily wet shaving. The brush on the back side, as shown in FIG. 11, includes a series of smooth silicone ridges arranged in a wave formation, intended to provide minimal abrasion and to maximize the pulsation energy transfer and the effectiveness of the dual-frequency (high-frequency and lower-frequency motor in combination) toning and low-frequency, muscle-relaxing functions.

Figure 12:
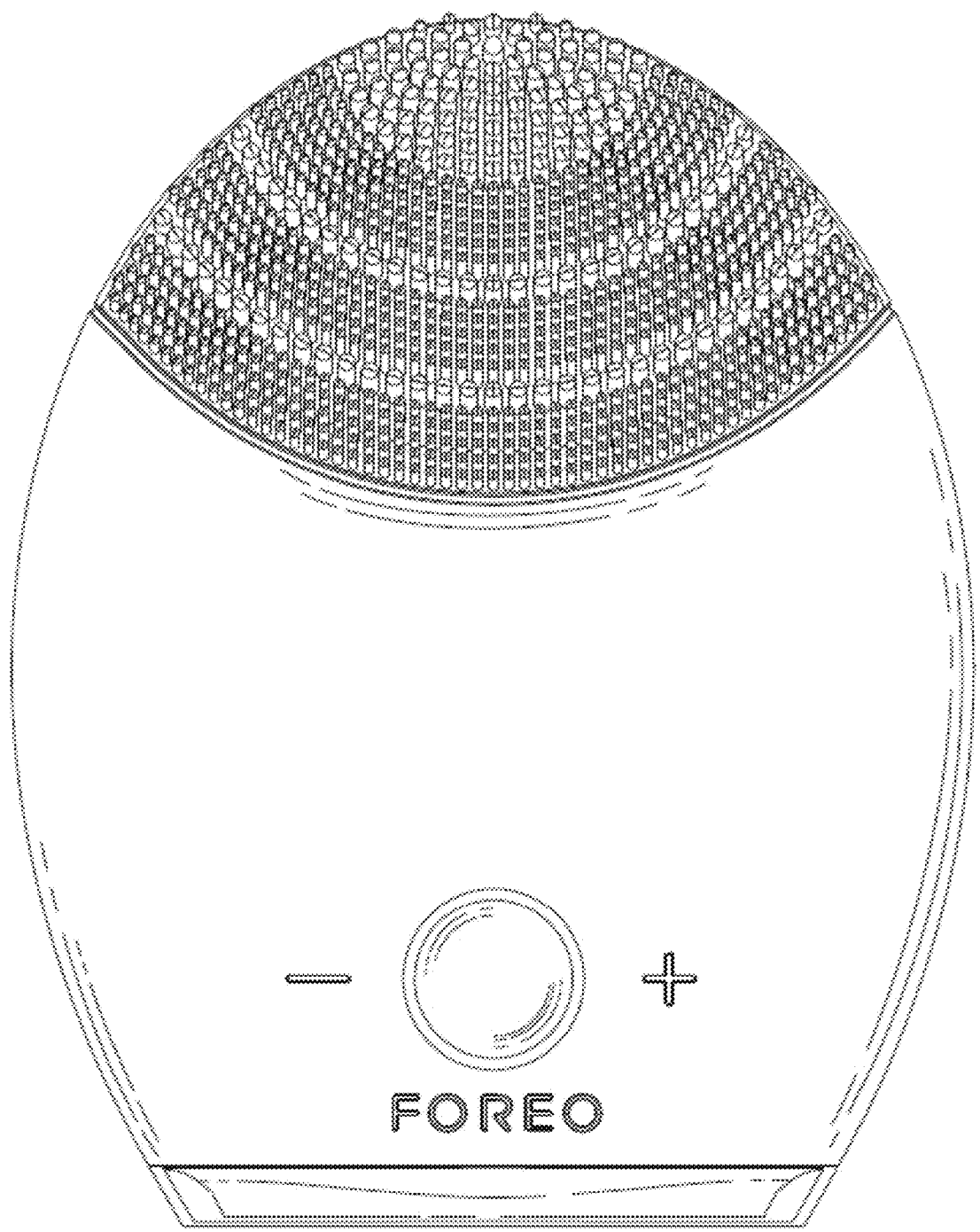
FIGS. 12 and 13 are views of one embodiment of a brush surface configuration for a skin cleanser.
Figure 13:
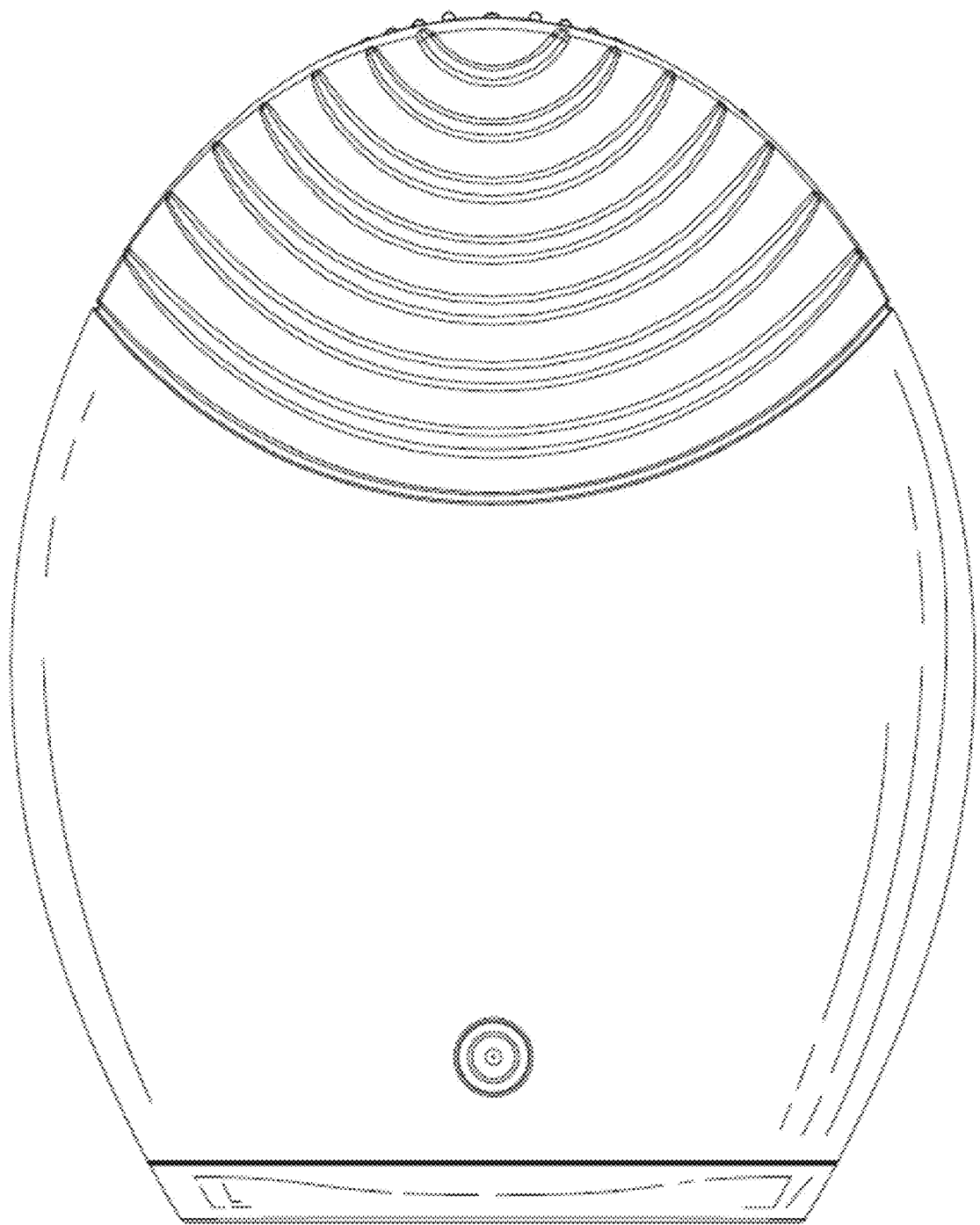

FIGS. 12 and 13 are views of one embodiment of a brush surface configuration for a skin cleanser. This brush configuration is specialized for skin with some oilier areas. The brush on the front side, as shown in FIG. 12, includes a series of thinner touch-points for gentle cleansing of non-oily or sensitive skin, with an area of thicker touch-points grouped towards the top of the cleanser, as well as two additional waves of thicker touch-points. Providing less flexibility than the thinner touch-points, these allow for stronger cleansing and the targeting of oilier areas and hard to-reach points around the nose, ears and hairline. The brush on the back side, as shown in FIG. 13, includes a series of smooth silicone ridges arranged in a wave formation, intended to provide minimal abrasion and maximize the pulsation energy transfer and the effectiveness of the dual-frequency toning and low-frequency, muscle-relaxing functions.

Figure 14:
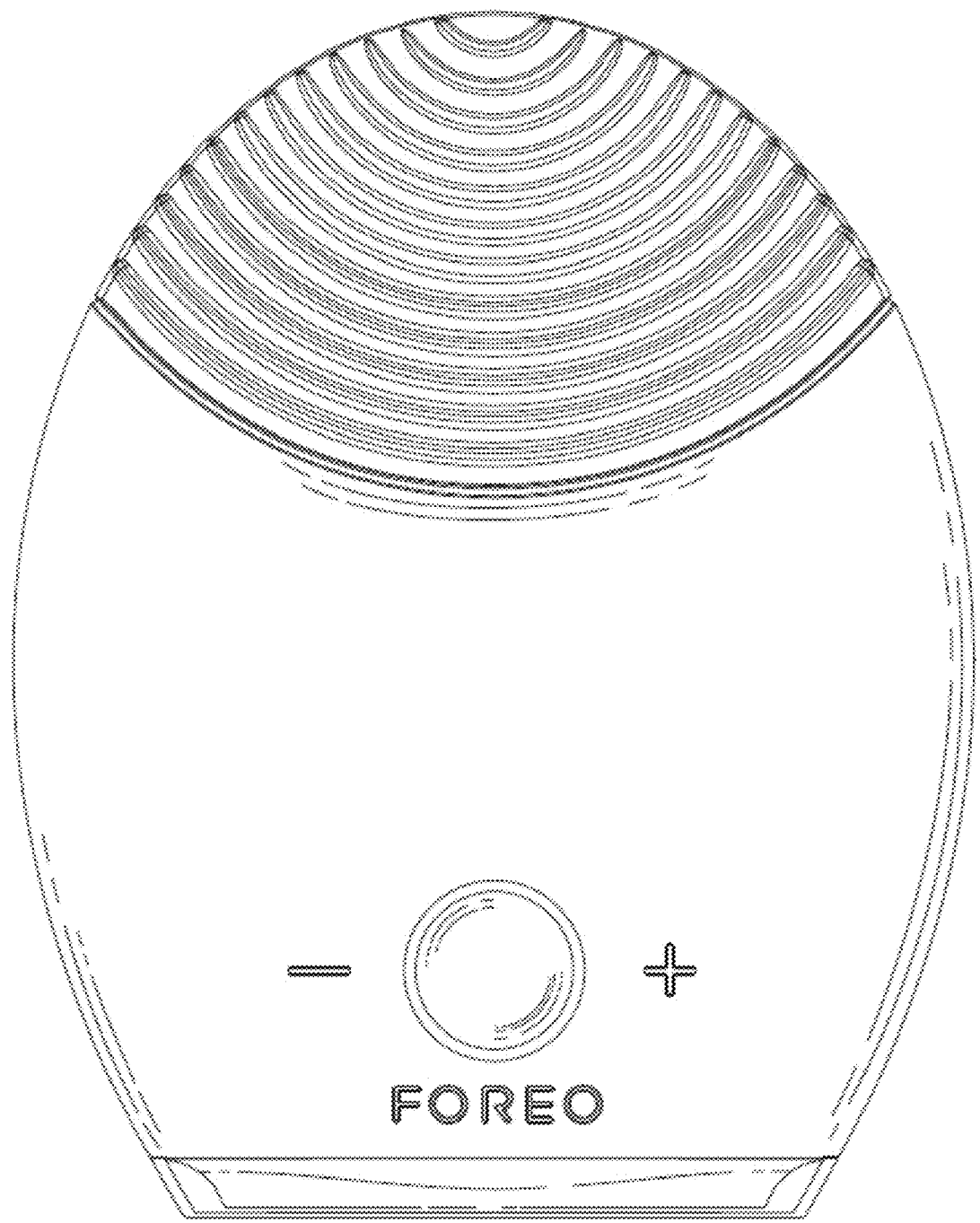
FIGS. 14 and 15 are views of one embodiment of a brush surface configuration fora skin cleanser.
Figure 15:
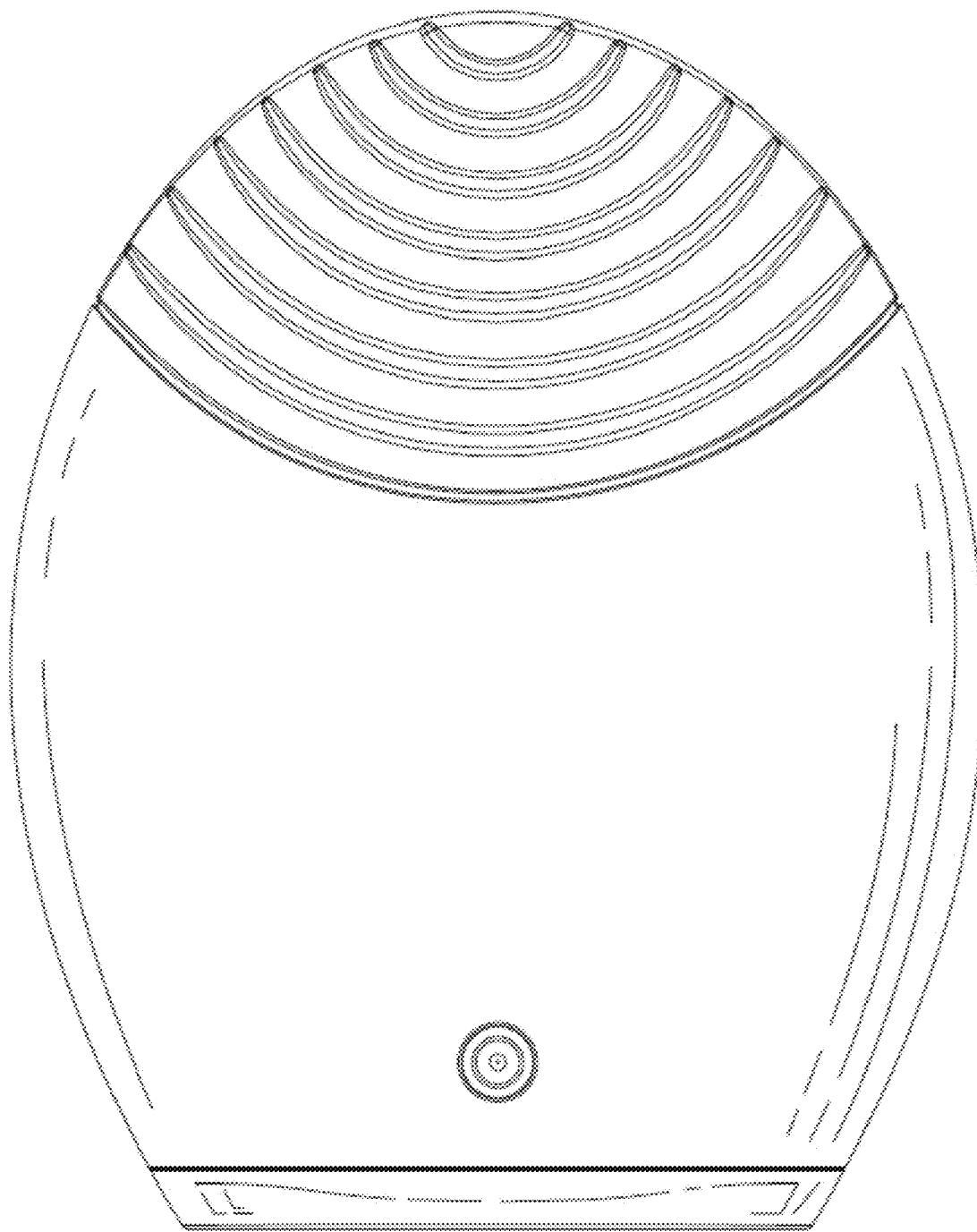

FIGS. 14 and 15 are views of one embodiment of a brush surface configuration for a skin cleanser. This brush configuration is specialized for sensitive skin. The brush on the front side, as shown in FIG. 14, includes a series of closely packed, smooth silicone ridges in a wave formation, designed to minimize abrasion and allow for the extra-gentle yet highly effective cleansing of even the most sensitive skin. The brush on the back-side, as shown in FIG. 15, includes a series of smooth silicone ridges arranged in a wave formation, intended to provide minimal abrasion and to maximize the pulsation energy transfer and the effectiveness of the dual-frequency toning and low-frequency, muscle-relaxing functions. The smooth silicone ridges on the front side in one embodiment are spaced closer to one another compared to the spacing of the ridges on the back-side. The ridges on the front side may be spaced between 10-60% closer together (e.g., 20%, 30%, 40%, 50%, etc. or values in between) relative to the spacing of the ridges on the back-side. In addition, the ridges on the front side are cushioned with additional space between the soft elastic surface and the plastic casing in order to provide with extra-gentle cleansing.

Figure 17:
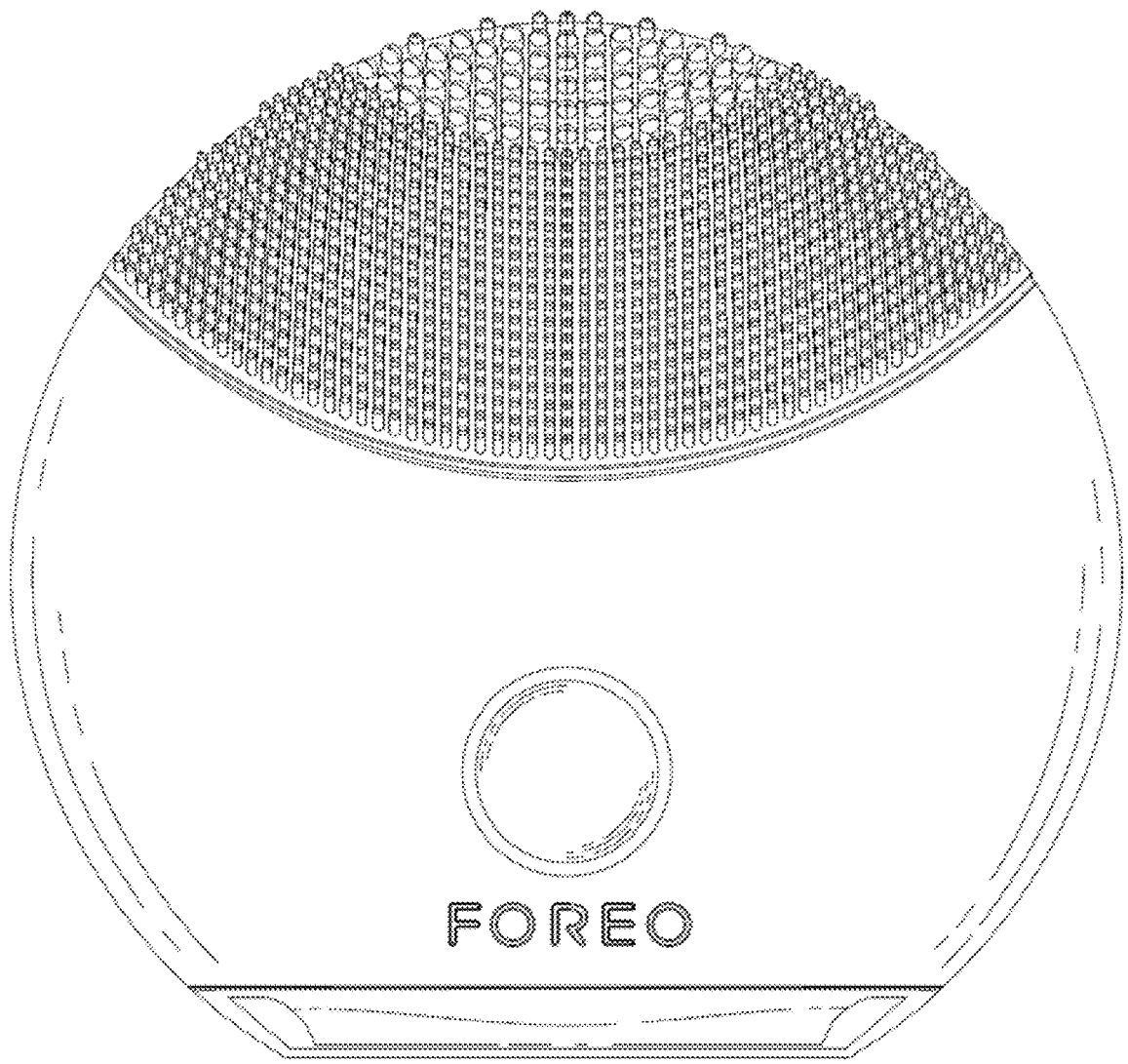
FIGS. 17 and 18 are views of one embodiment of a brash surface configuration for a skin cleanser.
Figure 18:
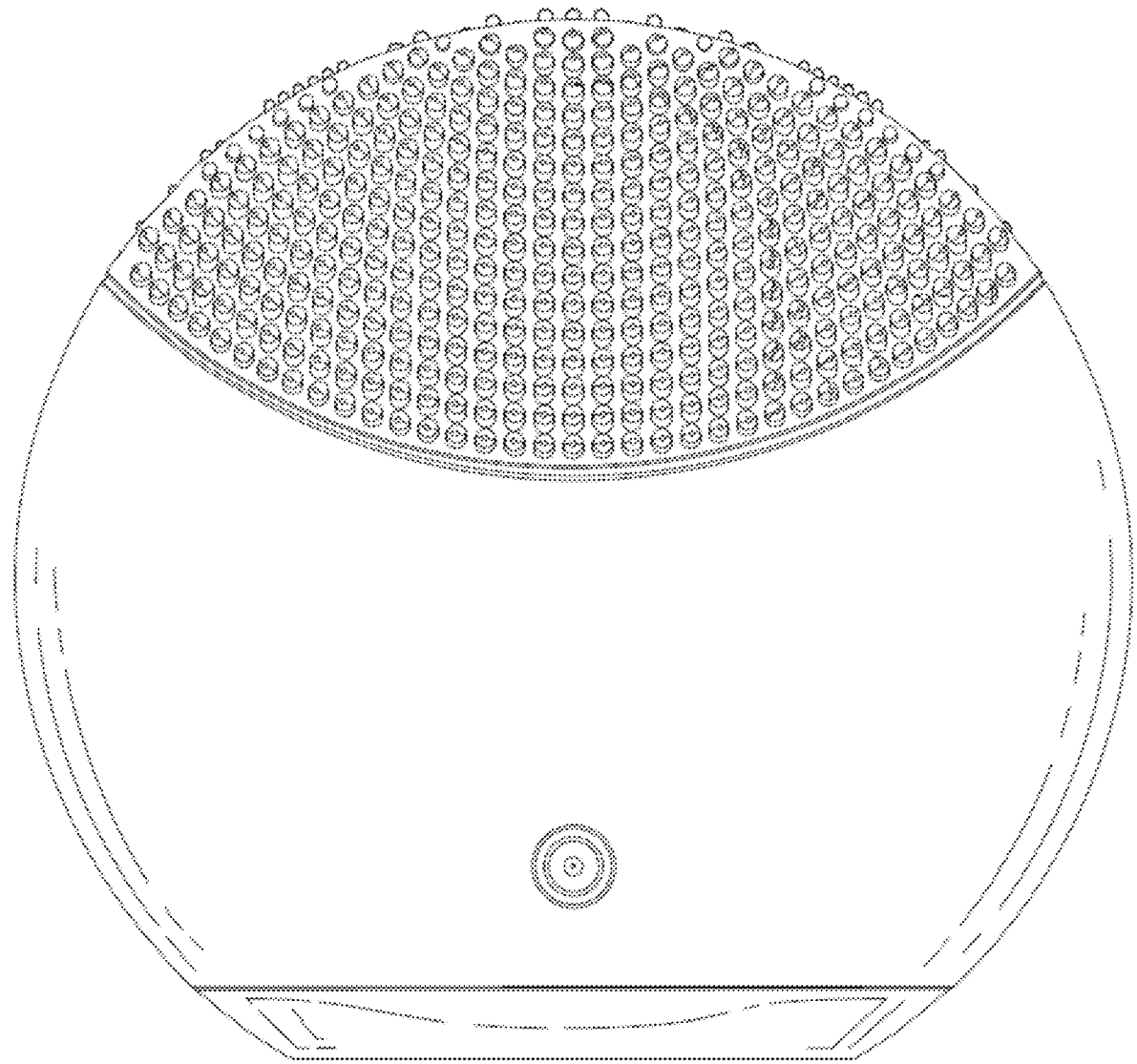

FIGS. 17 and 18 are views of one embodiment of a brush surface configuration for a skin cleanser. This brush surface configuration corresponds to the internal configuration shown in FIG. 1. The brush on the front side, as shown in FIG. 17, includes a series of thinner touch-points for gentle cleansing of non-oily or sensitive skin, with an area of thicker touch-points grouped towards the top of the cleanser. The brush on the back side, as shown in FIG. 18, provides a series of thicker touch-points allowing a deeper clean provided by the thicker touch-points to be applied to a larger area.

Figure 3:
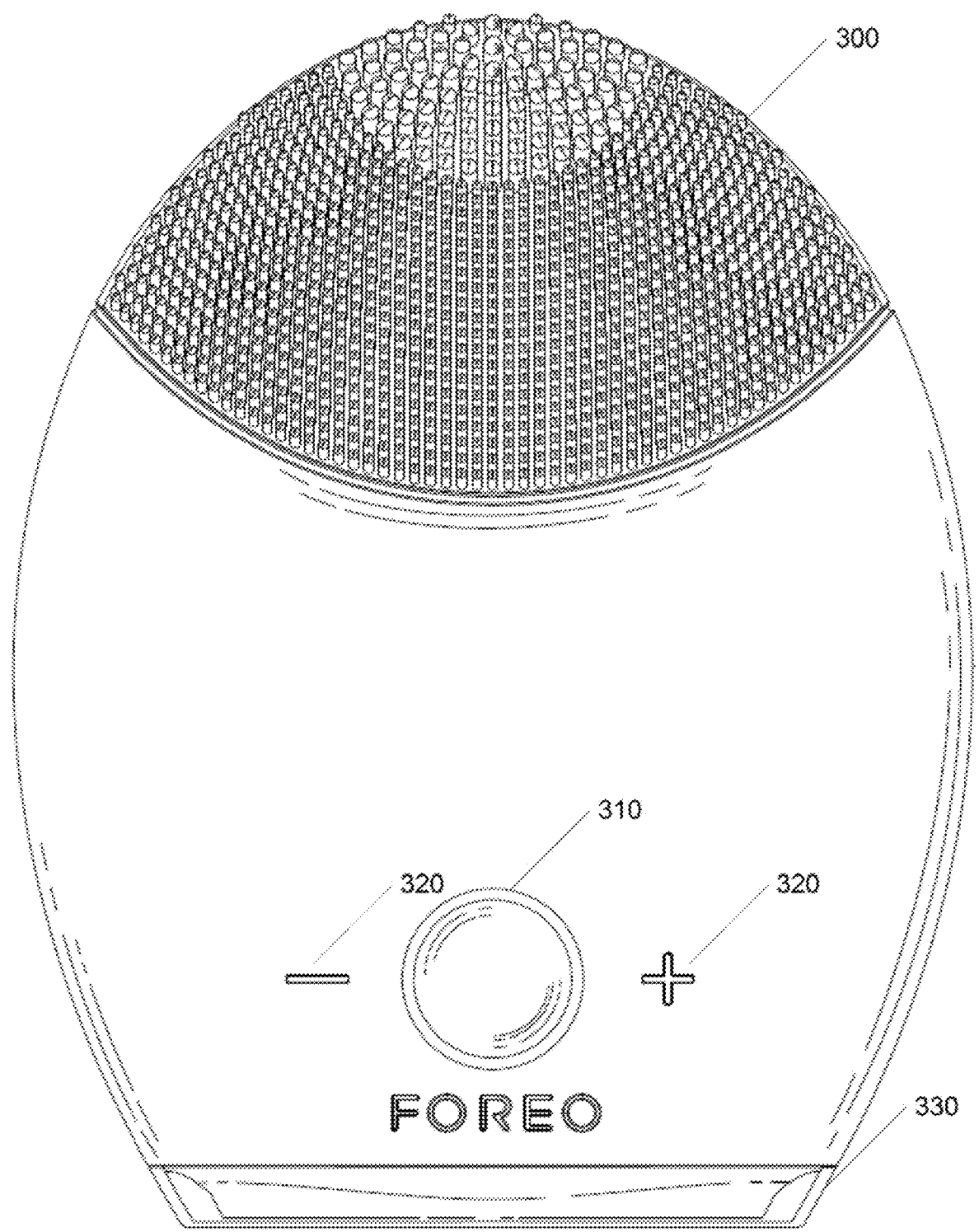
FIG. 3 is a front view of a skin cleanser, according to one embodiment.
Figure 4:
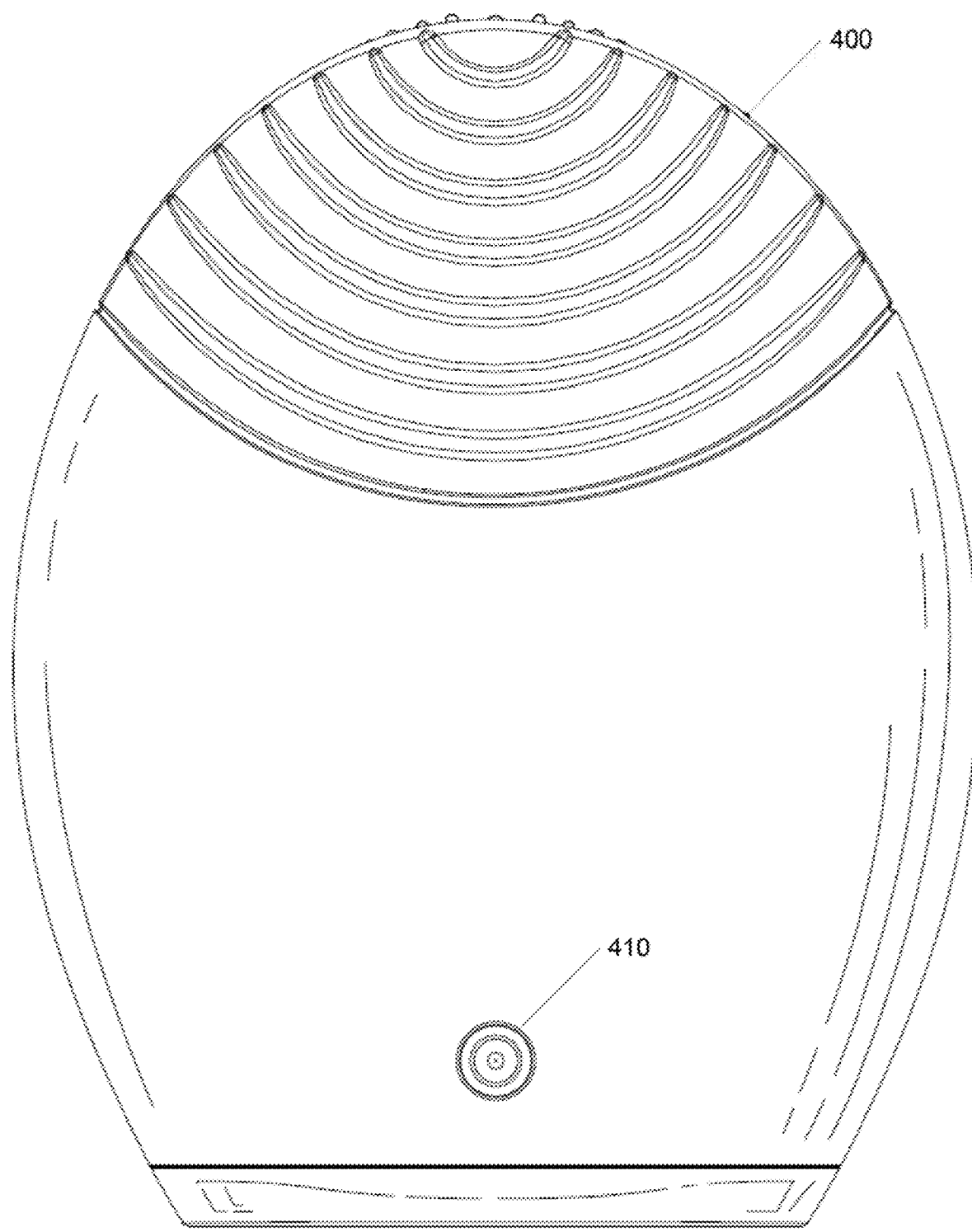
FIG. 4 is a back view of a skin cleanser, according to one embodiment.
Figure 5:
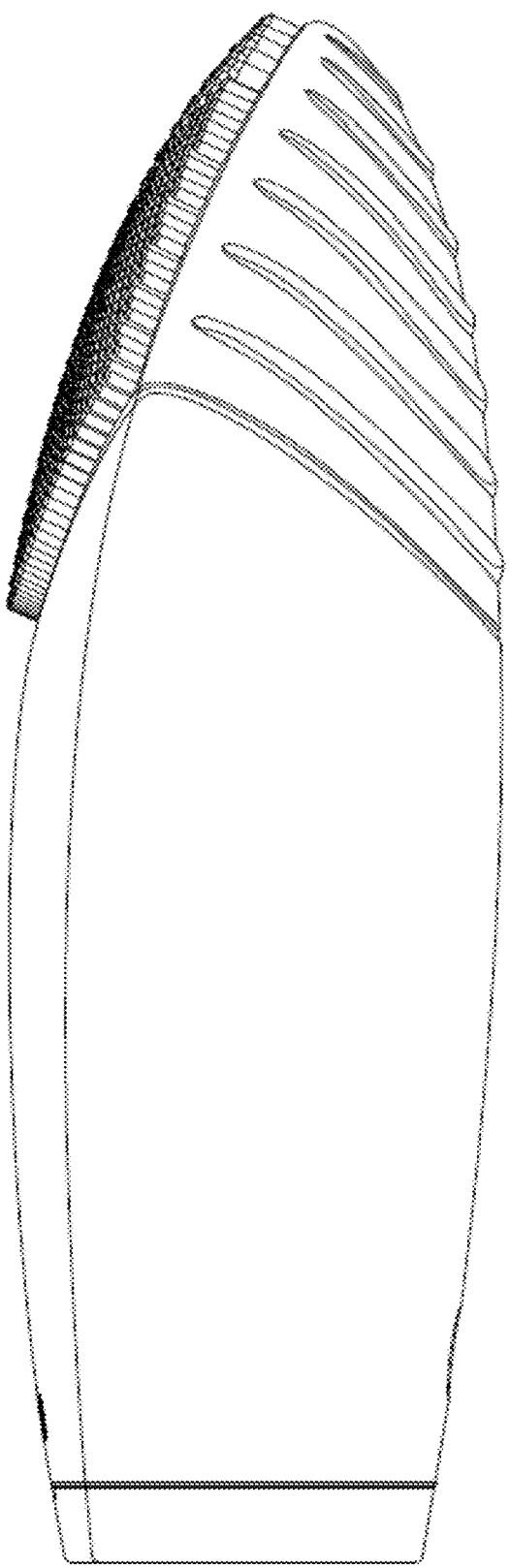
FIGS. 5 and 6 are side views of a skin cleanser, according to one embodiment.
Figure 6:
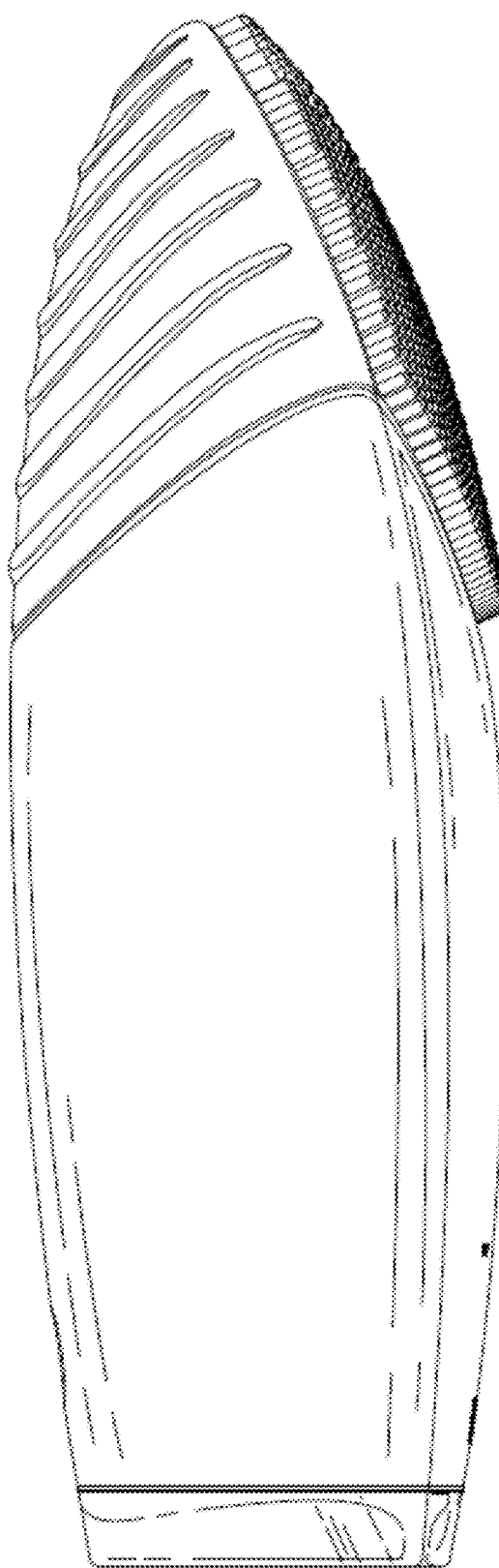
Figure 7:
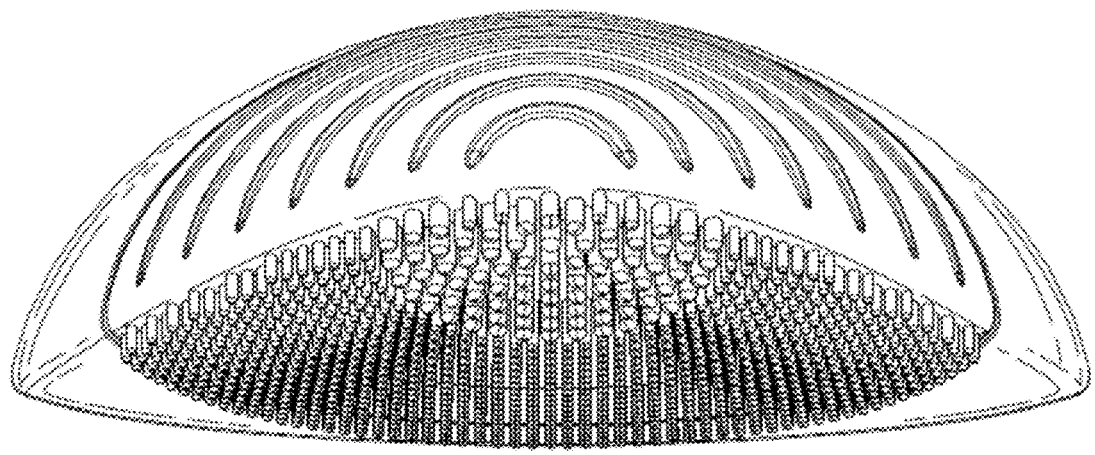
FIGS. 7 and 8 are top and bottom views of a skin cleanser, according to one embodiment.
Figure 8:
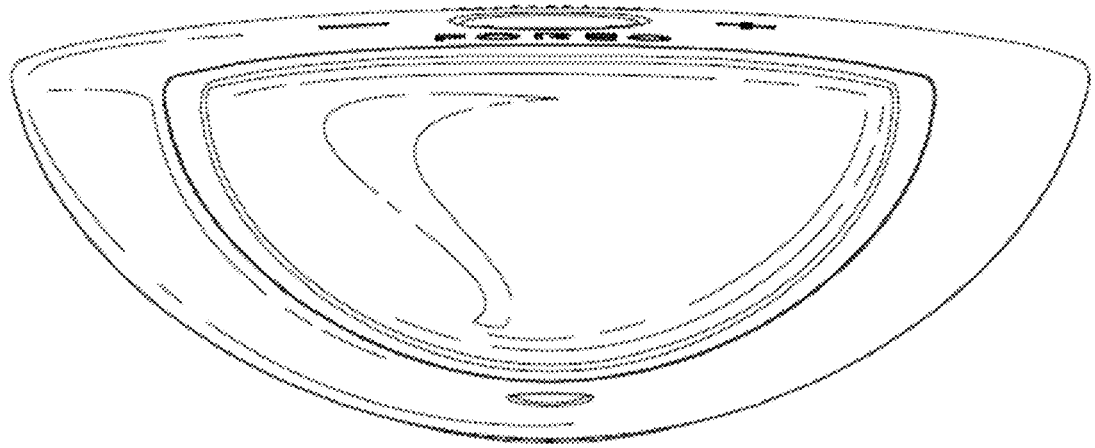
Figure 9:
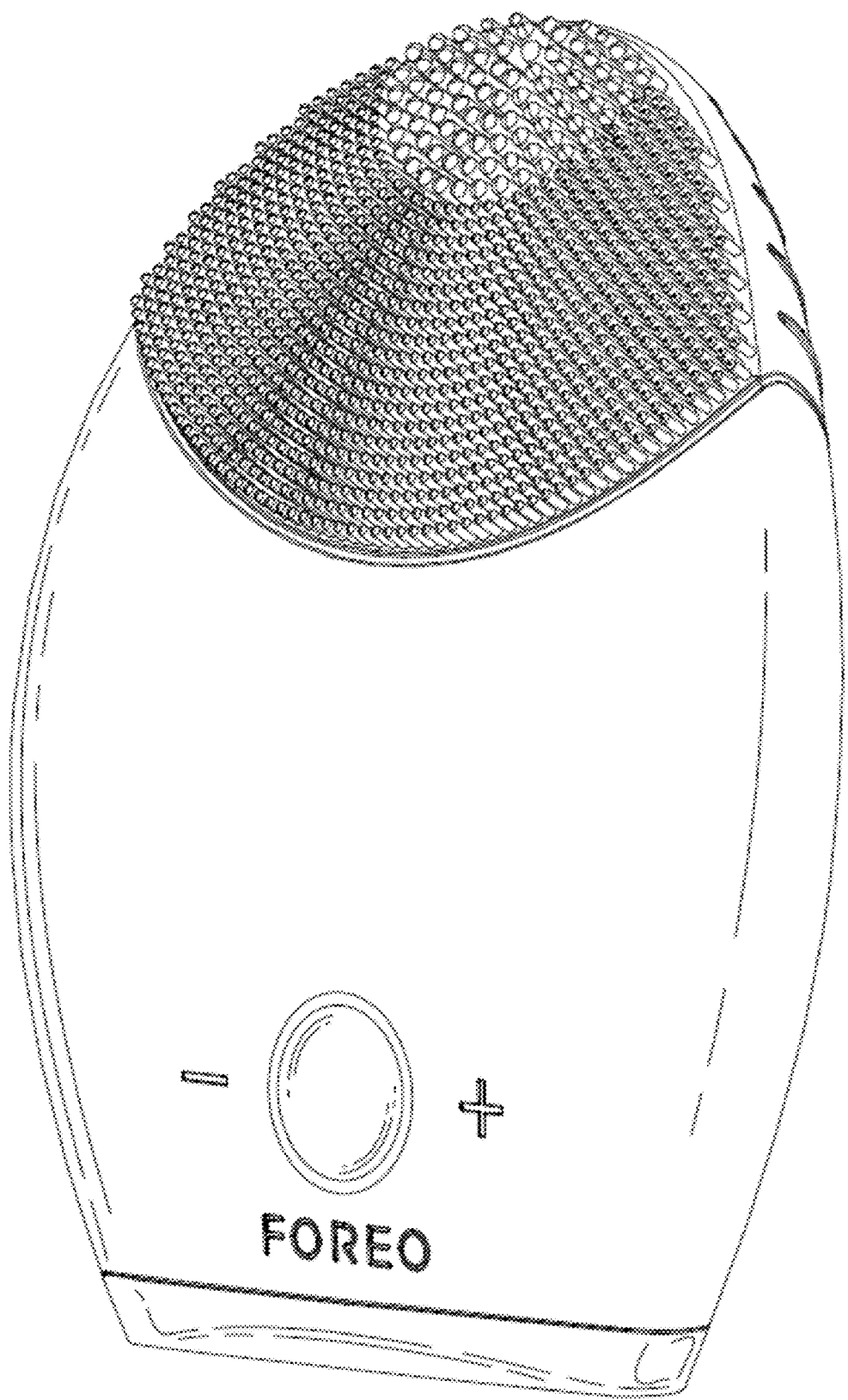
FIG. 9 is a perspective view of a skin cleanser, according to one embodiment.

FIGS. 3-15 and 17-18 are just some examples of different brush surface configurations matched to different skin types. Other designs for other skin types are also possible, such as a particular pattern for dry skin, for aging skin, for combination skin or T-zone skin (e.g., oilier around the forehead, nose, and chin), among others. In some embodiments, the front textured surface includes at least two different types of touch-points (e.g., thicker and thinner). The touch-points of a type can be grouped to provide a pattern. For example, FIG. 3 shows a group of thicker touch-points at the tip of the cleanser and a group of thinner touch-points below. Each pattern can correspond to a particular skin type (e.g., male, sensitive, oily, normal, etc.). In some embodiments, at least 10%, 20%, 30%, 40%, 50% of the front textured surface includes touch-points of a different type than the rest of the front textured surface.

The brush surface can also be designed to contour to the curves of the body or face. In one embodiment, one or more surfaces of the brush, e.g., the textured surfaces, are deformable or bendable. For example, where the textured surface is composed of silicone, the surface can compress or bend when pressed against the skin to mold to the surface of the skin for providing a deeper cleansing and for better cleaning of skin surfaces that are curved. In other embodiments, the textured surface can be designed to pivot relative to the brush or to include one or more portions that pivot such that the textured surface can mold to the shape of the skin.

Figure 16:
FIG. 16 is a skin analyzer, according to one embodiment.

FIG. 16 is a skin analyzer according to one embodiment. The skin analyzer is a handheld device capable of analyzing the skin of the user. The results of the skin analysis may be provided to the user to guide use of the skin cleanser, for example by measuring effectiveness and oiliness of the skin after use. The skin analyzer is encased in a body 1600 held by the operator of the skin analyzer. The skin analyzer includes sensors 1610 that sense the skin's condition, such as oil levels, moisture content, and dead skin cell levels. The results of the skin analysis may be communicated to the user by connecting the skin analyzer to a display or by wireless communication with a display or computer to direct the user in the use of a skin cleanser, such as whether the skin cleanser is being used too frequently or to show improvement of the skin over a period of time as the skin cleanser is applied. The skin analyzer may also provide the results of the analysis via an interface to the skin cleanser, which may be used to change the suggested frequency of applying the skin cleanser to portions of the user's face during cleansing. The cleanser can also include an interface to communicate with the skin analyzer, including sending information about how often it is used, what skin regimens or programs are used, etc.

In one embodiment, the skin analyzer can provide a diagnostic of the user's particular skincare needs, such as by indicating skin type (e.g., oily skin, oily skin in certain areas, sensitive skin, dry skin, dry in certain areas, male or female skin, normal skin, etc.) or by indicating specific details about the user's skin at different areas of the face or different times of day (e.g., tends to be dry in the morning, tends to be thin near the eye area, tends to be dry around the nose, etc.). The skin analyzer data can be used to design a program or skincare regimen specific to the user's skin. The program designed for a user's skin may be assessed by the user or by a third party, such as the manufacturer of the skin cleanser or analyzer, a beautician, a dermatologist or other medical personnel, etc. For example, information about the program can be transmitted via the interface of the skin analyzer or skin cleanser to a computer of the user or third party for review and possible revision. The program or regimen (possibly as revised by the user or third party) can be programmed to the controller of the skin cleanser according to the diagnostic of the user's particular skincare needs.

Additional features may also be included in the skin cleanser. In one embodiment, the skin cleanser includes a heat-emitting source located between the body and the textured surfaces. The heat-emitting source, when activated by the controller, heats the textured surfaces and may be used in conjunction with the oscillations of the touch-points. In a further embodiment, the skin cleanser includes a dosing mechanism integrated in the body of the device to dispense liquids or solid suspensions, such as for the delivery of silver nanoparticles, Vitamin E, etc. as described above. The dosing mechanism may include a reservoir, for example at the base of the skin cleanser, and a pump with an outlet to dispense contents of the reservoir to the textured surfaces or near the textured surfaces.

SUMMARY

The foregoing description of the embodiments of the invention has been presented for the purpose of illustration;

it is not intended to be exhaustive or to limit the invention to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention.

What is claimed is:

1. A skin cleanser having a skin cleanser body, comprising:
   a substantially flat base configured to stand unaided on a substantially flat surface, said skin cleanser body having a cross-sectional shape that is longer in a first direction substantially parallel to the base than in a second direction substantially parallel to the base;
   a silicone exterior covering substantially all of an exterior of said skin cleanser body, the silicone exterior having a textured surface area that is integrally formed with the silicon exterior, the textured surface area comprising a set of touch-points;
   a motor disposed within said skin cleanser laxly configured to produce pulsations of the skin cleanser; and
   at least one control disposed on said skin cleanser body configured to operate the motor.

2. The skin cleanser of claim 1, wherein the diameter of thee touch-points is between about 0.5 millimeters and about 2.5 millimeters.

3. The skin cleanser of claim 2, wherein the touch-points are integrally formed with the silicone exterior.

4. The skin cleanser of claim 1, wherein the base is substantially transparent.

5. The skin cleanser of claim 1, wherein the motor is operable to oscillate within the range of about 50 to 300 Hertz (Hz).

6. The skin cleanser of claim 1, wherein the textured surface area of touch-points is compressible to contour to a surface of a user's skin.

7. The skin cleanser of claim 1, wherein said skin cleanser body is configured to be held in a hand of a user with a thumb of the user resting against a first side of the silicone, exterior and fingers of the user resting on a second side of the silicone exterior.

8. The skin cleanser of claim 7, wherein the second side has a curvature and is configured to be held in the palm of a user's hand.

9. A skin cleanser having a skin cleanser body, comprising:
   a substantially flat base configured to stand unaided on a substantially flat surface, said skin cleanser laxly having a cross-sectional shape that is longer in a first direction substantially parallel to the base than in a second direction substantially parallel to the base;
   a silicone exterior covering substantially all of an exterior of said skin cleanser body, the silicone exterior comprising a set of touch-points integrally formed with the silicone exterior;
   a motor disposed within said skin cleanser body configured to produce pulsations of the skin cleanser; and
   at least one control disposed on said skin cleanser body configured to operate the motor.

10. The skin cleanser of claim 9, wherein the diameter of at least two touch-points of the set of touch-points is between about 0.5 millimeters and about 2.5 millimeters.

11. The skin cleanser of claim 10, wherein each touch-point of the set of touch-points has substantially the same diameter.

12. The skin cleanser of claim 11, wherein the silicone exterior comprises a second set of touch-points.

13. The skin cleanser of claim 12, wherein each touch-point of the second set of touch-points has substantially the same diameter.

14. The skin cleanser of claim 9, wherein the silicone exterior comprises a set of ridges.

15. The skin cleanser of claim 14, wherein the set of ridges includes at least four ridges.

16. The skin cleanser of claim 15, wherein at least a portion of each ridge of the set of ridges extends towards the base from an end of said skin cleanser body opposite the base.

17. A skirt cleanser having a skin cleanser body, comprising:
   a substantially flat base configured to stand unaided on a substantially flat surface, said skin cleanser body having a cross-sectional shape that is longer in a first direction substantially parallel to the base than in a second direction substantially parallel to the base;
   a silicone exterior covering substantially all of an exterior of said skin cleanser body, the silicone exterior comprising a set of touch-points; and
   a motor disposed within said skin cleanser body configured to produce pulsations of the skin cleanser.

18. The skin cleanser of claim 17, wherein the motor is operable to oscillate within the range of about 50 Hertz to about 300 Hertz.

19. The skin cleanser of claim 18, wherein the set of touch-points forms a substantially semi-circular pattern.

20. The skin cleanser of claim 19, wherein the silicone exterior comprises a second set of touch-points.

* * * * *